US010286182B2

(12) United States Patent
Sutermeister et al.

(10) Patent No.: US 10,286,182 B2
(45) Date of Patent: May 14, 2019

(54) RENAL CATHETER SHAFT DESIGN

(71) Applicant: Boston Scientific Scimed, Inc., Maple Grove, MN (US)

(72) Inventors: Derek Sutermeister, Ham Lake, MN (US); Cass Hanson, St. Paul, MN (US); Dan Quillin, Eden Prairie, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1141 days.

(21) Appl. No.: 14/076,769

(22) Filed: Nov. 11, 2013

(65) Prior Publication Data

US 2014/0135755 A1    May 15, 2014

Related U.S. Application Data

(60) Provisional application No. 61/725,246, filed on Nov. 12, 2012.

(51) Int. Cl.
*A61B 18/00* (2006.01)
*A61B 18/14* (2006.01)
*A61M 25/00* (2006.01)

(52) U.S. Cl.
CPC ..... *A61M 25/0026* (2013.01); *A61B 18/1492* (2013.01); *A61B 2018/00011* (2013.01); *A61B 2018/0022* (2013.01); *A61B 2018/00023* (2013.01); *A61B 2018/00035* (2013.01); *A61B 2018/00107* (2013.01); *A61B 2018/00238* (2013.01); *A61B 2018/00285* (2013.01); *A61B 2018/00345* (2013.01); *A61B 2018/00404* (2013.01); *A61B 2018/00434* (2013.01); *A61B 2018/00511* (2013.01);

(Continued)

(58) Field of Classification Search
CPC .. A61B 2018/0016; A61B 2018/00077; A61B 2018/00214; A61B 2018/00238; A61B 2018/1465; A61B 2018/147; A61B 2018/1472
See application file for complete search history.

(56) References Cited

U.S. PATENT DOCUMENTS 4,979,948 A * 12/1990 Geddes ............. A61B 18/1492
606/33
5,236,413 A * 8/1993 Feiring .................. A61F 11/00
604/103.01

(Continued)

*Primary Examiner* — Ronald Hupczey, Jr.

(57) ABSTRACT

A medical device for ablation of a target tissue is disclosed. The medical device includes a catheter assembly attached to a balloon for the ablation of the target tissue. The catheter assembly includes a proximal end and a distal end. The catheter assembly includes a plurality of individual shafts placed concentrically or adjacent to each other. Further, the plurality of individual shafts includes a respective lumen, wherein the lumens of the plurality of individual shafts can be configured to supply radio frequency (RF) energy to an RF transmitter placed inside the balloon and also to serve as the passageway for a fluid to travel within the balloon. The fluid flowing within the lumens of the catheter assembly can further help in expanding the balloon and transferring energy from the RF transmitter within the balloon to the ablation site via a plurality of windows attached.

14 Claims, 6 Drawing Sheets

(52) U.S. Cl.
CPC ............... *A61B 2018/00791* (2013.01); *A61B 2018/00821* (2013.01); *A61B 2018/1472* (2013.01)

(56) References Cited

U.S. PATENT DOCUMENTS

| | | | | |
|---|---|---|---|---|
| 5,797,903 | A * | 8/1998 | Swanson | A61L 29/085 600/374 |
| 5,891,136 | A * | 4/1999 | McGee | A61B 18/1492 600/374 |
| 6,001,094 | A * | 12/1999 | Edwards | A61N 1/403 606/41 |
| 6,673,296 | B2 * | 1/2004 | Hiraiwa | B29C 44/141 264/275 |
| 6,997,899 | B2 | 2/2006 | Scopton | |
| 7,422,587 | B2 * | 9/2008 | Bek | A61B 18/1492 128/898 |
| 7,736,362 | B2 * | 6/2010 | Eberl | A61B 18/1492 606/41 |
| 7,919,910 | B2 * | 4/2011 | Eidenschink | A61M 25/1038 310/311 |

* cited by examiner

RENAL CATHETER SHAFT DESIGN

CROSS-REFERENCE TO RELATED APPLICATIONS

This Application claims the benefit of and priority to U.S. Provisional Application No. 61/725,246, filed Nov. 12, 2012, the entire contents of which are herein incorporated by reference.

FIELD

This disclosure relates to a medical device for ablation of target tissues. More particularly, it relates to radio frequency (RF) ablation catheters with integrated cooling lumens.

BACKGROUND

Arterial hypertension is one of the most important causes of cardiovascular morbidity and mortality. A possible solution for this problem can be the use of an ablation procedure for ablation of tissues via delivery of radio-frequency (RF) energy.

Some of the existing renal artery RF ablation systems involve energy transfer via an inflated balloon that can be built on an Over-The-Wire (OTW) shaft platform. Some of these balloon concepts can include a fluid circulation loop or flow loops to provide cooling during the ablation cycle. Flow loops can be created to serve several different purposes i.e., temperature regulation, drug delivery, continuous monitoring, etc. The flow paths for the system can be created using several designs. While there can be several advantages to an OTW system, one of the main drawbacks of such catheters can be the difficulty in fine-tuning the fluid inlet and outlet flow rates. Understanding and controlling the inlet flow and the outlet flow (i.e., back pressure) is critical to the catheter system as it directly impacts balloon sizing.

An alternative to OTW catheter systems is the rapid exchange platform. In rapid exchange catheters, a guide wire is positioned adjacent to the inlet and outlet lumens. A rapid exchange port connects the guide wire lumen to the external surface of the catheter body. The rapid exchange port provides a means for quickly removing one type of catheter and threading a new catheter onto the guide wire while maintaining the guide wire in place relative to the target area. An example of a rapid exchange catheter is described in U.S. Pat. No. 6,997,899, which is hereby incorporated by reference. Compared to OTW catheters, rapid exchange catheters allow the use of a shorter guide wire and facilitate control of inlet and outlet flow rates. A drawback of rapid exchange catheters is that, compared to the OTW catheters, the rapid exchange configuration requires a larger catheter profile in order to obtain a given flow rate.

Thus, there exists a need for a medical device with multi-shaft and multi-lumen design that can allow independent fine-tuning of the inlet and outlet lumen sizes while providing a separate lumen that can be accessed to form a rapid-exchange wire port. Likewise, there is a need to maximize inflow and outflow cross-sectional areas for fluidic transport while maintaining the lowest possible device profile. In RF ablation catheters, there is also a need to establish circulation in the catheter balloon while maintaining concentricity of the balloon with respect to the RF transmitter.

Without limiting the scope of the invention, a brief summary of some of the claimed embodiments of the invention is provided below. Additional details of the summarized embodiments of the invention and/or additional embodiments of the invention can be found in the detailed description of the invention.

A brief abstract of the technical disclosure in the specification is provided as well for the purposes of complying with 37 C.F.R. 1.72. The abstract is not intended to be used for interpreting the scope of the claims.

All US patents and applications and all other published documents mentioned anywhere in this application are incorporated herein by reference in their entirety.

SUMMARY

In at least one embodiment, the invention is directed to a catheter assembly for ablation of a target tissue comprising an elongated catheter body having a proximal end portion and a distal end portion. The elongated catheter body further includes a plurality of individual shafts placed concentric or adjacent to one other. Further, the plurality of individual shafts includes an interior wall and an exterior wall, wherein the interior wall of each plurality of individual shafts defines a respective lumen. The catheter assembly further includes a balloon positioned at the distal end portion of the elongated catheter body. The balloon is configured to be inflated between an expanded state and an unexpanded state with the use of a fluid flow along the lumen defined by at least one of the plurality of individual shafts. Further, the catheter assembly includes a radio frequency (RF) transmitter mounted on the exterior wall of at least one of the plurality of individual shafts such that the RF transmitter while bathed in an ionic fluid, such as saline, generates ionic energy, which is directed through the balloon to a desired location or locations upon supply of an external energy.

In at least one embodiment, the invention is directed to a catheter assembly for ablation of a target tissue comprising an elongated catheter body having a proximal end portion and a distal end portion. The elongated catheter body further includes a first innermost shaft, a second middle shaft, and a third outermost shaft. The shafts are positioned independently and concentrically with respect to one another from a central axis. Further, each shaft defines an interior wall and exterior wall, wherein the interior wall of each shaft defines a respective lumen. The catheter assembly further includes a balloon, which comprises a top coat on at least a portion of the outer surface of the balloon and a plurality of balloon windows. The balloon can be positioned at the distal end portion of the elongated catheter body so as to inflate between an expanded state and unexpanded state with the use of a fluid flow. Further, the catheter assembly includes an RF transmitter mounted on the exterior wall of at least one of the plurality of individual shafts, such that the RF transmitter can get conductively coupled with the balloon via conductive fluid.

BRIEF DESCRIPTION OF THE FIGURES

The invention and the following detailed description of certain embodiments thereof can be understood with reference to the following figures.

DETAILED DESCRIPTION

While this invention can be embodied in many different forms, specific embodiments of the invention are described in detail herein. This description is an exemplification of the principles of the invention and is not intended to limit the invention to the particular embodiments illustrated.

For the purposes of this disclosure, like reference numerals in the figures shall refer to like features unless otherwise indicated.

Various aspects of the invention are depicted in the figures. Elements depicted in one figure can be combined with and/or substituted for elements depicted in another figure as desired.

The terms proximal and distal described in relation to various devices, apparatuses, and components as discussed in the subsequent text of the present invention are referred with a point of reference. The point of reference, as used in this description, is a perspective of an operator. The operator can be a surgeon, a physician, a nurse, a doctor, a technician, and the like, who can perform the procedure of delivery and placement of the disclosed system/device into the patient's body as described in the present invention. The term proximal refers to an area or portion that is closer or closest to the operator during a placement procedure. The term distal refers to an area or portion that is further or farthest from the operator.

Figure 1:
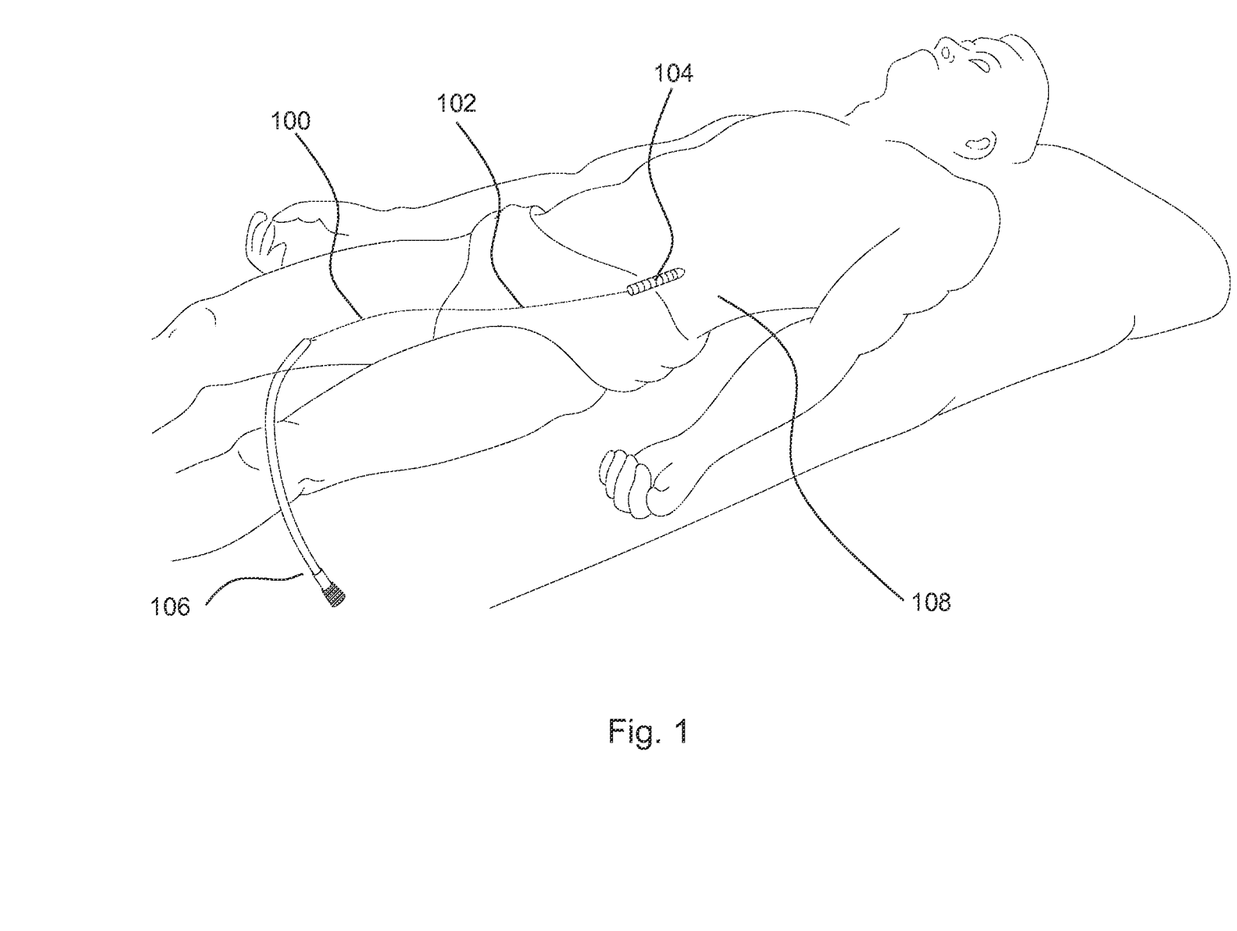
FIG. 1 is a perspective view of a system having a catheter and a medical balloon operationally positioned in a body of a patient.

Referring now to FIG. 1, a catheter assembly 100 having an elongated catheter body 102, a balloon 104, and a syringe 106 is shown for performing a medical procedure at an internal treatment site 108 of a patient. A pump or other suitable device can be used in place of the syringe 106. The catheter assembly 100 is to be positioned inside a patient's body to treat a lesion in a body artery of a human patient. Although the catheter assembly 100 is capable of performing a medical procedure in a lower body artery such as a renal artery, those skilled in the pertinent art will quickly recognize that the use of the catheter assembly 100 as described herein is not limited to an artery, but can be used in vascular conduits and other ductal systems such as a bile duct, a urinary tract and the like throughout the human body. FIG. 1 shows the catheter assembly 100 used in a human body. It is to be appreciated that the medical system can also be used in non-humans such as animals, if desired. As used herein, the term "biological material" and its derivatives includes, but is not limited to, cellular matter including tissue (diseased, healthy or otherwise), deposits such as cholesterol and calcium deposits, and lesions which, for example, can consist of cellular matter and/or deposits.

FIG. 1 illustrates an exemplary embodiment of femoral access to a bodily location. However, other approaches of access through different body locations other than those shown in FIG. 1, including, but not limited to, radial access via the arm, are within the scope of the present invention.

Figure 2A:
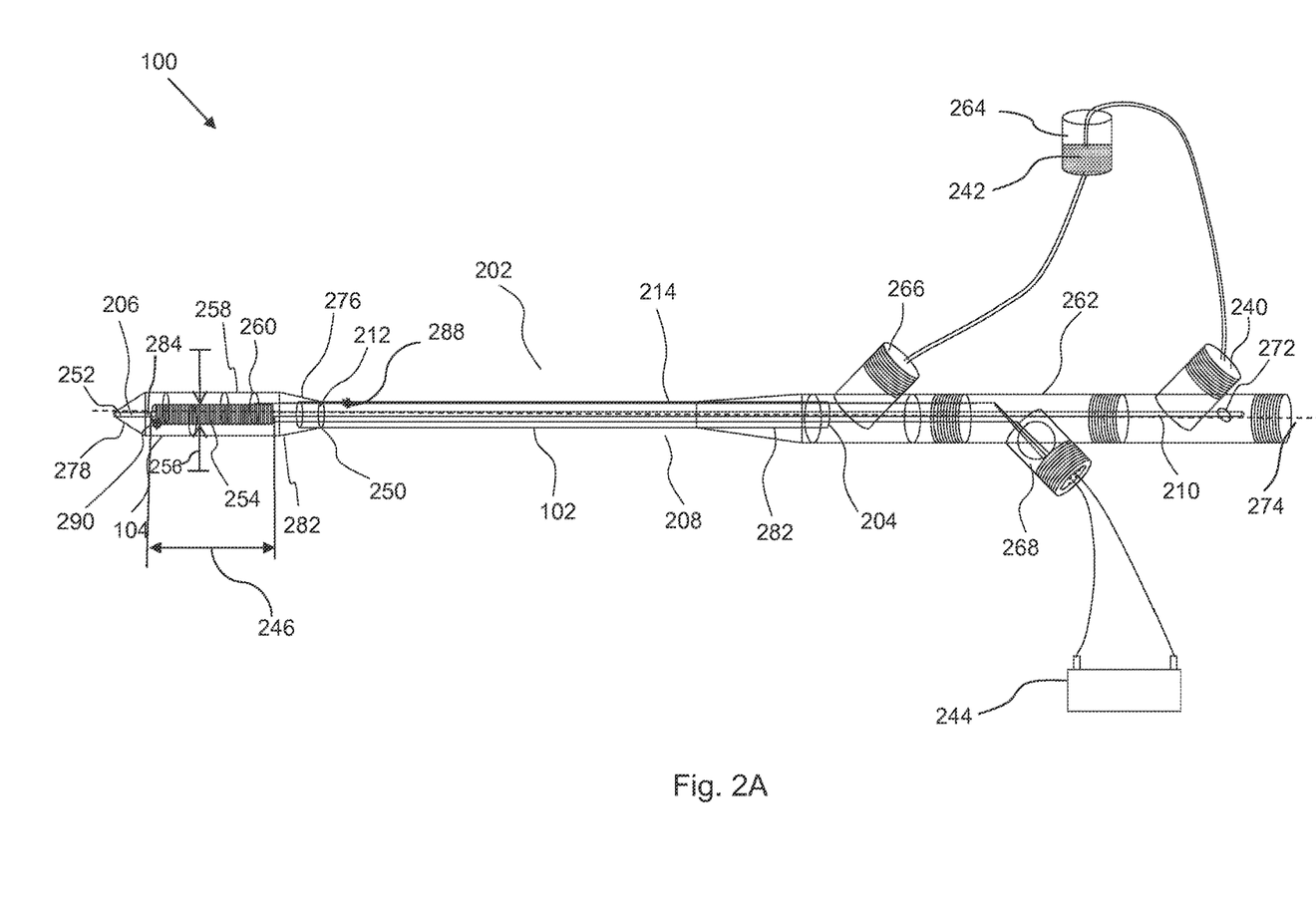
FIG. 2A is a front view schematic diagram of a system having a catheter and a medical balloon with concentrically placed shafts.
Figure 2B:
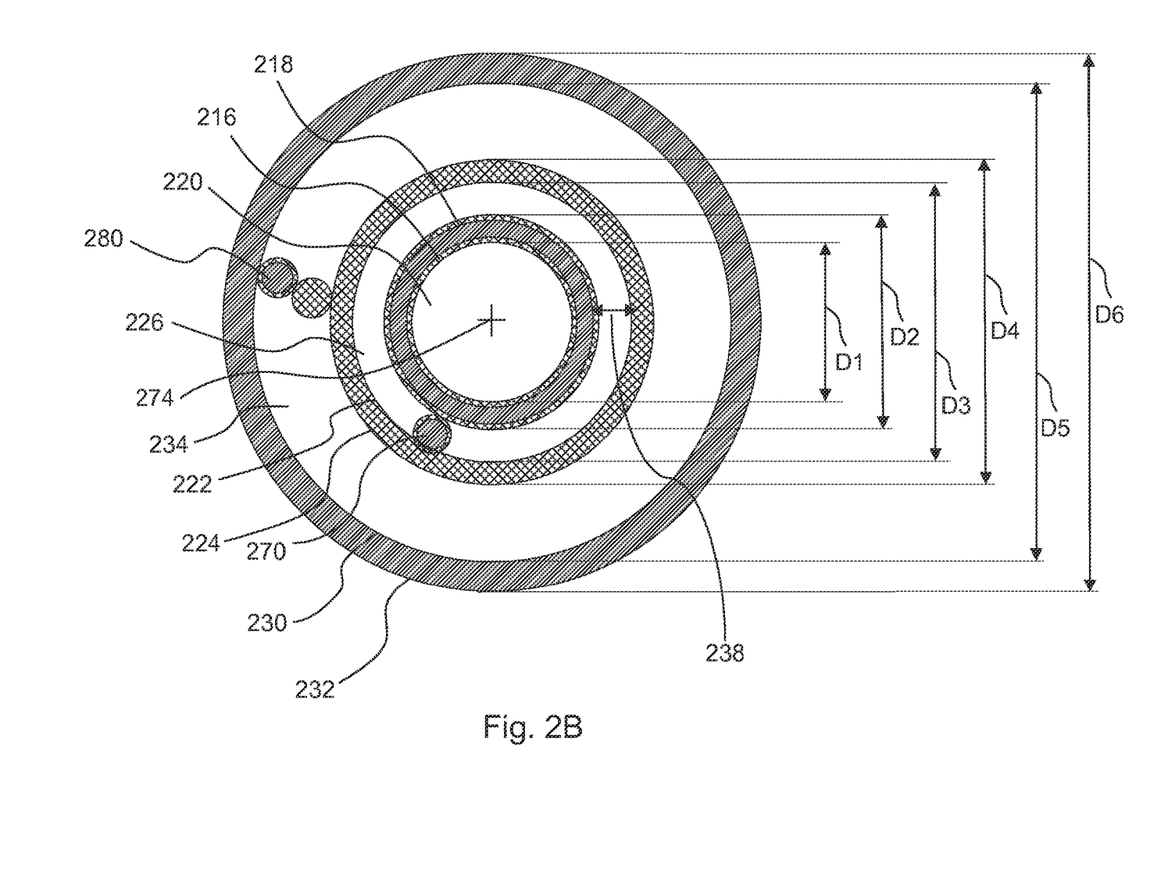
FIG. 2B is a cross-sectional view of the catheter with concentrically placed shafts.

Referring now to FIG. 2A, a front view of the catheter assembly 100 comprising the elongated catheter body 102 and the balloon 104 is shown. FIG. 2B illustrates a cross-sectional view of the elongated catheter body 102.

In an embodiment, the catheter assembly 100 can be configured to include the elongated catheter body 102 having a proximal end portion 204 and a distal end portion 206. In an embodiment, the elongated catheter body 102 includes a plurality of individual shafts 208 placed concentrically around a central axis 274. The balloon 104 is disposed at the distal end portion 206 and an RF transmitter 254 is mounted on at least one of the plurality of shafts 208 toward the distal end portion 206 of the elongated catheter body 102. The RF transmitter 254 is conductively coupled with the balloon 104, via conductive fluid 242, so as to transfer ionic energy to the balloon 104 upon application of an external energy. The RF transmitter 254 can be coupled to an external energy source 244. The external energy source 244 can be an energy generator capable of supplying energy to the balloon 104 via the RF transmitter 254. The catheter assembly 100 can be coupled to a fluid reservoir 264. The fluid reservoir 264 can include a fluid 242 that can be circulated inside the elongated catheter body 102. The fluid 242 can serve various functions including acting as a conduit for energy transfer from the RF transmitter 254 to the balloon 104, regulate balloon 104 pressure, and regulate balloon 104 temperature through fluid flow.

In the illustrated embodiment, each shaft from the plurality of shafts 208 can have a corresponding individual axis, thereby defining a tri-axial configuration. In an embodiment, the central axis 274 can be a common axis formed due to overlapping of each individual axis of the plurality of individual shafts 208. In an embodiment, the plurality of shafts 208 can include a first shaft 210, a second shaft 212, and a third shaft 214. In an embodiment, the first shaft 210 can be placed as an innermost shaft, the second shaft 212 can be placed as a middle shaft between the first shaft 210 and the third shaft 214, and the third shaft 214 can be placed as an outermost shaft such that the first shaft 210, the second shaft 212, and the third shaft 214 are positioned concentrically. The catheter assembly 100 can be so designed that a length and a cross section of each of the plurality of individual shafts 208 can influence an inflow back pressure and an outflow back pressure at a given flow rate for the fluid 242 such that the flow rate of the fluid 242 can be maintained at a same level at which the fluid 242 enters the catheter assembly and the fluid 242 exits the catheter assembly. Exemplary dimensions of the first shaft 210, the second shaft 212, and the third shaft 214 are explained herein. However, it should be understood that the dimensions and shaft arrangement can differ for various embodiments.

The first shaft 210 includes an interior surface 216 and an exterior surface 218. In an embodiment, the interior surface 216 can define a lumen 220. The lumen 220 can have a width D1. In an embodiment, the width D1 of the interior surface 216 can vary based on the requirement. The lumen 220 can be used for carrying a guide wire 272. The guide wire 272 can be configured to guide the catheter assembly 100 through the body of the patient to the target site 108. The guide wire 272 can have a thickness 286. In an embodiment, the thickness 286 can vary from 0.008 to 0.019 inches. In an embodiment, the thickness 286 can be 0.014 inches. In an embodiment, the thickness 286 can vary based on the requirements. The exterior surface 218 can define a distal end 252 at the distal end portion 206 of the elongated catheter body 102. The exterior surface 218 can define a dimension having a width D2 along the central axis 274. In an embodiment, the width D2 of the exterior surface 218 can range from 0.020 to 0.024 inches. In an embodiment, the width D2 of the exterior surface 218 can be 0.022 inches. In an embodiment, the width D2 of the exterior surface 218 can vary based on the requirement.

In an embodiment, the second shaft 212 can be placed around the first shaft 210. The second shaft 212 can include an interior surface 222 and an exterior surface 224. In an embodiment, the interior surface 222 can define a lumen 226 such that the first shaft 210 can be disposed into the lumen 226. The lumen 226 can have a width D3. In an embodiment, the width D3 can range from 0.035 to 0.045 inches. In an embodiment, the width D3 can be 0.034 inches. In an embodiment, the width D3 of the interior surface 222 can vary based on the requirement. The exterior surface 224 can define a dimension having a width D4 along the central axis 274. In an embodiment, the width D4 can range from 0.030 to 0.040 inches. In an embodiment, the width D4 can be 0.040 inches. In an embodiment, the width D4 of the exterior surface 224 can vary based on the requirement. In an embodiment, the interior surface 222 of the second shaft 212 and the exterior surface 218 of the first shaft 210 can define an inflow lumen 226 between them. The inflow lumen 226 can be configured for allowing the fluid 242 to flow from the proximal end portion 204 toward the balloon 104 of the catheter assembly 100. In an embodiment, the inflow lumen 226 can have a width 238. In an embodiment, the width 238 can vary from 0.002 to 0.010 inches. In an embodiment, the width 238 can be 0.006 inches. In an embodiment, the width or volume of the inflow lumen 226 can vary based on the requirements.

In an embodiment, when the fluid 242 is circulated inside the catheter assembly 100, the flow rate of the fluid 242 can be in a range of 18-22 ml/minute. In an embodiment, the flow rate of the fluid 242 can be 20 ml/minute. In the illustrated embodiment, the inflow lumen 226 is defined as that between the first shaft 210 and the middle shaft 212 such that the inflow lumen can extend up to the distal end 252 of the exterior surface 218 such that the inflow lumen 226 can be in communication with the balloon 104. In an embodiment, the inflow lumen 226 extends up to an inflow manifold 240 at the proximal end portion 204 of the catheter assembly 100. The inflow manifold 240 can be configured for serving as an inlet for the fluid 242 into the catheter assembly 100.

In accordance with the invention, the third shaft 214 can be configured to surround the second shaft 212. The third shaft 214 can include an interior surface 230 and an exterior surface 232. The interior surface 230 can define a lumen 234 for disposing the first shaft 210 and the second shaft 212. In an embodiment, the lumen 234 can have a width D5. In an embodiment, the width D5 can vary from 0.045 to 0.055 inches. In an embodiment, the width D5 can be 0.051 inches. In an embodiment, the width D5 can vary based on the requirement. The exterior surface 232 of the third shaft 214 can define a distal end 250. The exterior surface 232 can define a dimension having a width D6 along the central axis 274. In an embodiment, the width D6 can vary from 0.055 to 0.065 inches. In an embodiment, the width D6 can be 0.061 inches. In an embodiment, the width D6 can vary based on the requirement. The interior surface 230 can be configured to define a lumen 234 such that the second shaft 212 can be disposed into the lumen 234. In the illustrated embodiment, the first shaft 210 can be disposed into the lumen 226 defined by the second shaft 212, and the assembly of the second shaft 212 and the first shaft 210 can be disposed into the lumen 234 of the third shaft 214. The third shaft 214 can include a thermocouple 288 configured for monitoring a temperature of the fluid 242. The thermocouple 288 can be made up of copper and constantan thermocouple welded tip covered using, for example, 0.010" polyethylene terephthalate (PET) heat shrink polymer or a thermoset epoxy compound. The PET or epoxy compound shields the welded thermocouple tip from RF interference.

The interior surface 230 of the third shaft 214 and the exterior surface 224 of the second shaft 212 can define an outflow lumen 234 between them. In an embodiment, the catheter assembly 100 can be fabricated so that the second shaft 212 and the third shaft 214 can define a specific length and a specific cross-section for achieving and maintaining an internal balloon pressure at the specific flow rate of the fluid 242. In an embodiment, the flow rate of the fluid 242 can be in a range of 18-22 ml/minute. In an embodiment, the flow rate of the fluid 242 can be 20 ml/minute. In the illustrated embodiment, the outflow lumen 234 is defined between the third shaft 214 and the middle shaft 212 such that the outflow lumen 234 can extend up to the distal end 250 of the exterior surface 232. The outflow lumen 234 can allow the fluid 242 to flow from the balloon 104 toward the proximal end portion 204 of the elongated catheter body 102. In an embodiment, the outflow lumen 234 can be 0.050 to 0.060 inches. In an embodiment, the width D5 of the interior surface 230, the width D6 of the exterior surface 232, and the outflow lumen 234 can vary based on the requirements. In an embodiment, the outflow lumen 234 extends up to an outflow manifold 266 at the proximal end portion 204 of the catheter assembly 100. The outflow manifold 266 can be configured for serving as an outlet for the fluid 242 out of the catheter assembly 100.

The catheter assembly 100 further includes the balloon 104, wherein the balloon 104 can be an inflatable balloon 104 that can be inflated from an unexpanded state to an expanded state. The balloon 104 can have a proximal end portion 276 and a distal end portion 278. The balloon 104 can be attached to the elongated catheter body 102 so that the proximal end portion 276 of the balloon 104 is attached to the distal end 250 of the exterior surface 232 of the third shaft 214. The distal end portion 278 of the balloon 104 can be coupled to the distal end 252 of the exterior surface 218 of the first shaft 210.

The balloon 104 can be configured for ablation of the target site 108. The balloon 104 can include an electrically insulative top coat 258 spread across an entire exterior surface 282 of the balloon 104. In an embodiment, the balloon 104 can include a plurality of balloon windows 260 such that the RF transmitter 254 is operably coupled to the plurality of balloon windows 260 via conductive fluid 242 so as to transfer energy to the plurality of balloon windows 260 from the external energy source 244. The plurality of balloon windows 260 is an assembly of ionically permeable structures that can be positioned at various places on the balloon 104 so as to direct the generated ionic energy to the desired location or locations. The electrically insulative top coat 258 can be configured to block the generated ionic energy from the RF transmitter 254 while allowing the ionic energy to pass through the plurality of balloon windows 260 such that the ionic energy can be used for ablation of the target site 108.

The catheter assembly 100 further includes the RF transmitter 254 mounted on the exterior surface 224 of the second shaft 212. The RF transmitter 254 can define a distal end 284 such that the second shaft 212 terminates at the distal end 284. The RF transmitter 254 can be conductively coupled with the balloon 104. In an embodiment, the RF transmitter 254 can be a coiled wire or ribbon. In an embodiment, the RF transmitter 254 can have a thickness 256 that can vary from 0.002 to 0.009 inches. In an embodiment, the thickness 256 of the RF transmitter 254 can be 0.004 inches. In an embodiment, the thickness 256 of the RF transmitter 254 can vary based on the requirements. In an embodiment, the RF transmitter 254 can define a length 246. In an embodiment, the length 246 can vary from 1.5 mm to 2.5 cm. In an embodiment, the length 246 can be 2 cm. In an embodiment, the length 246 can vary based on the requirements. The RF transmitter 254 can be composed of metals including at least one of copper, silver, and the like. In an embodiment, the RF transmitter 254 can be composed of 97% copper with a coating of 3% silver. In an embodiment, the RF transmitter 254 can be enclosed within the balloon 104. The RF transmitter 254 can be mounted over the second shaft 212 and the balloon 104 is positioned such that the distal end portion 278 of the balloon 104 can be in contact with the distal end 252 of the exterior surface 218 of the first shaft 210 and the proximal end portion 276 of the balloon 104 can be in contact with the distal end 250 of the exterior surface 232 of the third shaft 214. This arrangement disposes the RF transmitter 254 inside the exterior surface 282 of the balloon 104, while allowing unhindered access to fluid flow inlet and outlet lumens.

In an embodiment, thermocouple wires 280 can be positioned proximate to the RF transmitter 254 and can be operably coupled to the thermocouple 288 such as to monitor temperature of the fluid 242 inside the catheter assembly 100 during outflow. The power wire 270 runs through the inflow lumen 226 the thermocouple wires 280 run through the outflow lumen 234.

The proximal end portion 204 of the elongated catheter body 102 can be attached to a fluid management manifold 262. In an embodiment, the fluid management manifold 262 includes the inflow manifold 240 and the outflow manifold 266. In an embodiment, the fluid management manifold 262 can include a thermocouple and power jack 268 (referred to as jack 268 hereafter) that can be configured to be operatively coupled to the power wire 270 and the thermocouple wires 280. The jack 268 can send energy to the RF transmitter 254 via the power wire 270. In an embodiment, the jack 268 can be coupled to the external energy source 244. The thermocouple wires 280 also run from the jack 268 to the thermocouple 288. The power wire 270 can be positioned so as to be operatively coupled via a weld 290 to a RF transmitter 254 so as to provide RF energy to the fluid 242.

The balloon 104 can be configured to perform ablation of a tissue using RF energy. For ablation of the tissue, the power jack 268 provides RF energy to the RF transmitter 254 placed inside the balloon 104 via the power wire 270 running from the power jack 268 to the balloon 104. The RF energy is converted to ionic energy at the surface of the RF transmitter 254 placed inside the balloon 104, which is blocked from leaving the balloon 104 by the electrically insulative top coat 258 except via the plurality of balloon windows 260. In an embodiment, the source of energy generation can be the external energy source 244.

There is a possibility that during the process of ablation, the plurality of balloon windows 260 and balloon surface 282 may be heated to an undesired temperature and hence, cooling of the balloon 104 may be required. In an embodiment, the fluid 242 can be proposed to enter from the inflow manifold 240. The fluid 242 can then be transferred to the balloon 104 via the inflow lumen 226. In an embodiment, the inflow lumen 226 can define a path for the fluid flow across the lumen 226 such that the fluid enters the proximal portion 204 of the elongated catheter body 102. In an embodiment, the fluid 242, after cooling and inflating the balloon 104, can be brought out of the catheter assembly 100 via the outflow lumen 234 and finally out of the catheter assembly 100 via the outflow manifold 266. In an embodiment, the outflow lumen 234 can define a path for the fluid 242 to exit from the distal portion 278 of the balloon 104 and finally out of the catheter body 102.

The first shaft 210, the second shaft 212, and the third shaft 214 can be connected at the proximal end portion 204 of the catheter assembly 100. In an embodiment, the first shaft 210, the second shaft 212, and the third shaft 214 can be connected at the proximal end portion 204 by ultra violet (UV) glue. The second shaft 212 can be free at the distal end portion 206 of the catheter assembly 100.

In an embodiment, the RF transmitter 254 can be used to deliver energy which is directed to the target site 108 via fluid 242. Energy flow through the RF transmitter 254 is controlled by the material, the cross-sectional area, the length of the RF transmitter, and the overall design of the RF transmitter 254. The transmission of energy from the RF transmitter 254 to the fluid 242 is controlled by the surface area of the RF transmitter 254 in contact with the fluid 242. In an embodiment, the RF transmitter 254 can be positioned over the second shaft 212.

In accordance with the invention, the process of ablation of the tissue starts with the generation of ionic energy at the surface of RF transmitter 254, wherein ionic energy of the fluid 242 can be transferred to the target site 108 via the plurality of windows 260.

In an embodiment, a specific pressure drop can be calculated for a given length of each of the plurality of shafts 208 and a given cross-section of each of the plurality of shafts 208 for controlled internal balloon pressure. In an embodiment, the catheter assembly 100 can be fabricated so that the second shaft 212 and third shaft 214 can define a specific length and a specific cross-section for achieving and maintaining the pre-calculated pressure drop of the fluid 242 across the catheter assembly 100 through the outflow lumen 234.

In an embodiment, since the balloon 104 can become heated to an undesired temperature during ablation procedure, the cooling of the balloon 104 may be required. The fluid 242 can enter the catheter assembly 100 from the inflow manifold 240 at the proximal end portion 204 of the elongated catheter body 102 and move toward the distal end portion 206 such that the fluid 242 enters the distal end portion 278 of the balloon 104 at the distal end 252, thereby filling the balloon distally to proximally. The air inside the catheter assembly 100 can be pushed out while the fluid 242 is entering the balloon 104. As the balloon is filled distally to proximally the fluid 242 can inflate the balloon 104, cool the balloon 104, and can exit through the outflow lumen 234

The inflow lumen 226 and the outflow lumen 234 can be so designed that the fluid 242 enters the balloon 104 from the inflow lumen 226 and exits through outflow lumen 234, leaving it expanded for ablation of the target site 108.

In an embodiment, the inflow lumen 226 and the outflow lumen 234 can define a flow path for the fluid 242. The fluid 242 enters the proximal end portion 204 of the elongated catheter body 102 and exits at the distal end 252, thereby filling the balloon 104 to an expanded state distally to proximally along an axial direction and further configured to flow out via the outflow lumen 234 so that at least one of the plurality of shafts 208 are sized to define a controlled outflow pressure drop causing the balloon 104 to inflate in a controlled manner. Outflow pressure drop is determined by the equation:

$$\Delta p = \frac{128 \mu Q L}{\pi D^4}$$

where $\Delta p$ is the pressure drop, $\mu$ is the fluid viscosity, Q is the volumetric flow rate, L is the lumen length, and D is the lumen diameter. Lumen sizes may be defined mathematically through a pressure drop. In some embodiments, flow rate may be regulated by controlling balloon pressure. Balloon pressure can be controlled by a pressure control sensor, or by controlling volumetric inflows and outflows, or by monitoring variation in approach curvatures during balloon inflation. In some embodiments, pressure relief is built in the balloon. In at least one embodiment, a contrast containing media is incorporated into the inflation fluid.

In an embodiment, the fluid 242 can be brought out of the catheter assembly 100 travelling via the outflow lumen 234 and finally out of the catheter assembly 100 via the outflow manifold 266. In an embodiment, the fluid used can be saline.

In an embodiment, the fluid 242 can function as at least one of a conduction medium between the RF transmitter 254 and the balloon window 260 for the transmission of the energy, maintaining pressure within the balloon 104, and can be used as a coolant within the catheter assembly 100.

Figure 3A:
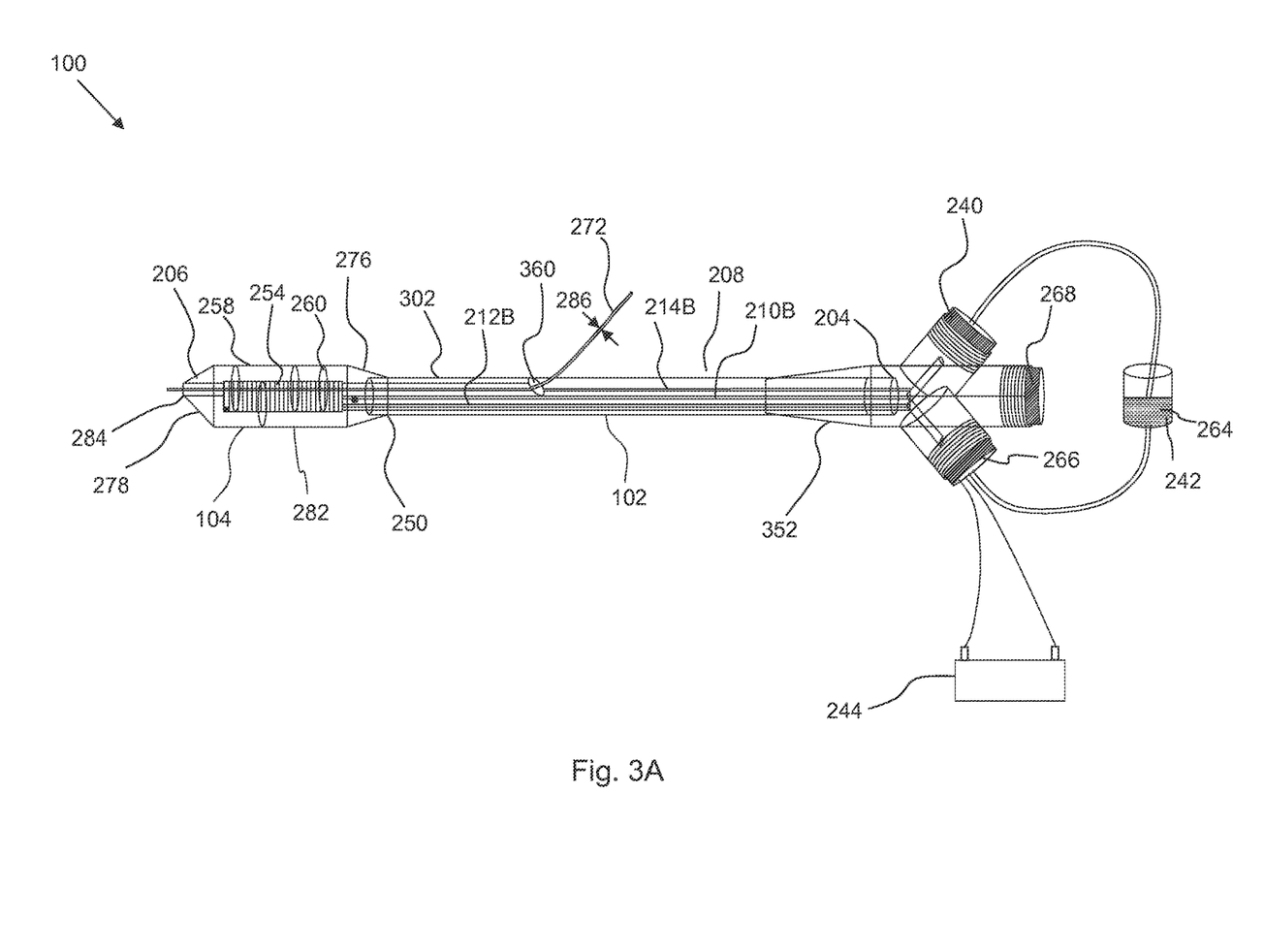
FIG. 3A is a front view schematic diagram of a system having a catheter and a medical balloon with adjacently placed shafts.
Figure 3B:
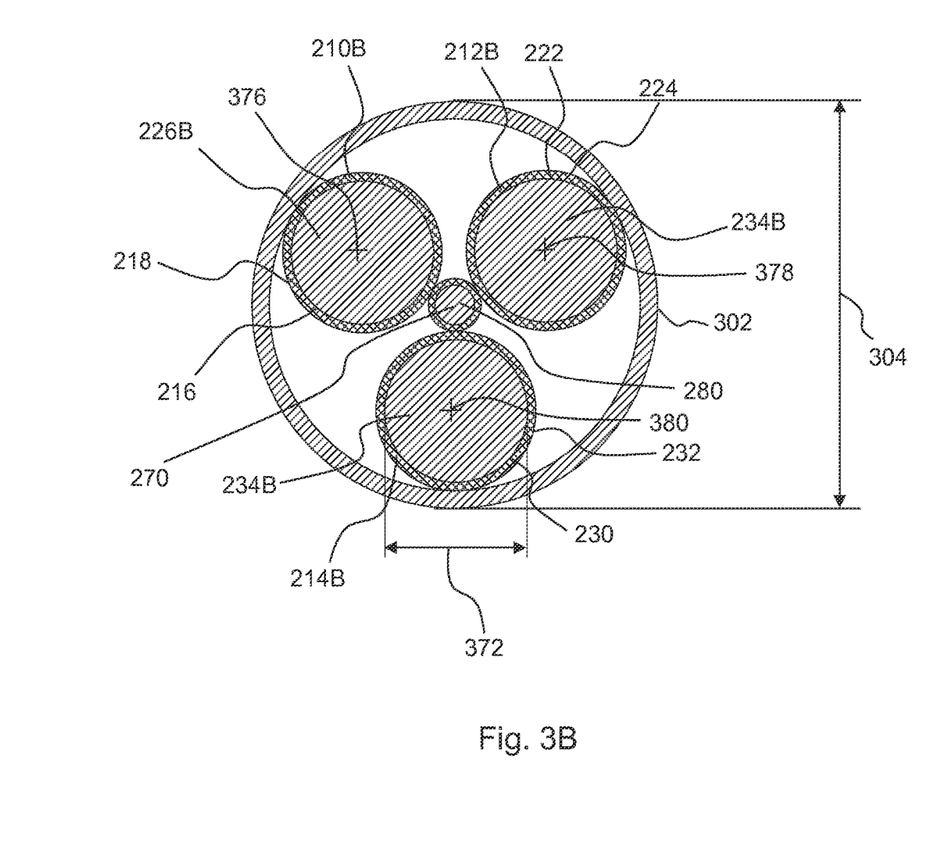
FIG. 3B is a cross-sectional view of the catheter with adjacent shafts.

FIG. 3A is a front view schematic diagram of the catheter assembly 100 comprising the elongated catheter body 102 and the balloon 104, wherein the plurality of shafts 208 can be placed adjacently. FIG. 3B illustrates a cross-sectional view of the elongated catheter body 102 of FIG. 3A.

In an embodiment, the catheter assembly 100 can be fabricated so that the first shaft 210B, the second shaft 212B, and the third shaft 214B can be placed adjacently so that the first shaft 210B can define the inflow lumen 226B, the second shaft 212B can define the outflow lumen 234B, and the third shaft 214B can carry the guidewire 272. The power wire 270, and the thermocouple wires 280 can be placed between the first shaft 210B, the second shaft 212B, and the third shaft 214B.

In an embodiment, the catheter assembly 100 can include an elongated catheter body 102, which can include an exterior wall 302. The exterior wall 302 can have a diameter 304. In an embodiment, the diameter 304 can vary from 0.060 to 0.070 inches. In an embodiment, the diameter 304 can be 0.065 inches. In an embodiment, the diameter 304 can vary based on the requirements. In an embodiment, the elongated catheter body 102 includes the plurality of individual shafts 208 placed adjacently. Further, the plurality of individual shafts 208 can include the first shaft 210B, the second shaft 212B, and the third shaft 214B.

In an embodiment, the first shaft 210B can be configured around an axis 376 such that the first shaft extends from the proximal end portion 204 to the distal end portion 206 of the catheter assembly 100. The lumen of the first shaft 210B can function as the inflow lumen 226B.

In an embodiment, the second shaft 212B can be configured around an axis 378 that can be parallel to the axis 376 so that the second shaft 212B can be placed adjacent to the shaft 210B. The lumen of the second shaft 212B can be designed to function as the outflow lumen 234B.

In an embodiment, the third shaft 214B can be configured around an axis 380 that can be parallel to the axis 376 and the axis 378 so that the first shaft 210B, the second shaft 212B, and the third shaft 214B can be placed adjacently and define the tri-axial configuration. In an embodiment, the lumen 234B of third shaft 214B can carry the guidewire 272.

In an embodiment, the lumen 234B of third shaft 214B can define a diameter 372 wherein, the diameter 372 can vary from 0.009 to 0.019 inches. In an embodiment, the diameter 372 can vary based on the requirements. In an embodiment, the guide wire 272 can be inserted within the lumen 234 of the third shaft 214 via an opening 360. The opening 360 can be configured in the exterior wall 302 of the elongated catheter body 102 to create a rapid exchange wire port.

The catheter assembly 100 further includes the balloon 104. The balloon 104 can be an inflatable balloon with the distal end portion 278 and the proximal end portion 276. The balloon 104 can be attached to the elongated catheter body 102 such that the proximal end portion 276 of the balloon 104 is attached to the distal end 250 of exterior wall 302 and the distal end portion 278 of the balloon 104 is attached to the exterior surface 232 of the third shaft 214B. The catheter assembly 100 further includes the RF transmitter 254 mounted on the exterior surface 218 of the first shaft 210B and exterior surface 232 of the third shaft 214B. The RF transmitter 254 can be structured in a similar manner as described with reference to FIGS. 2A-2B and can function in a similar manner. In an embodiment, the RF transmitter 254 can be a coiled wire or ribbon. The RF transmitter 254 can be composed of metals including at least one of copper, silver, and the like. In an embodiment, the RF transmitter 254 can be composed of 97% copper with a coating of 3% silver.

FIGS. 2A-2B describe the catheter assembly 100, wherein the first shaft 210, the second shaft 212, and the third shaft 214 can be placed concentrically to each other with their each individual axis coinciding to form the central axis 274. FIGS. 3A-3B describe the catheter assembly 100 wherein the first shaft 210B, the second shaft 212B, and the third shaft 214B can be placed adjacently, wherein the axis 376, the axis 378, and the axis 380 can be parallel to each other, so that the plurality of shafts 208 can be placed adjacent to each other. In the tri-axial configuration, wherein the plurality of shafts 208 are placed concentric to each other then, each shaft of the plurality of shafts 208 can be formed along the central axis 274. In the tri-axial configuration, wherein the plurality of shafts 208 is placed concentric to each other then, at least one of the shafts from the plurality of shafts 208 can be centralized. For example, by centralizing the second shaft 212, the RF transmitter 254 is centralized. This implies that the radial distance for the RF transmitter 254 to the balloon 104 is consistent for each of the plurality of balloon windows 260 on the balloon 104. An equal radial distance results in uniform energy distribution throughout the balloon 104.

Figure 4:
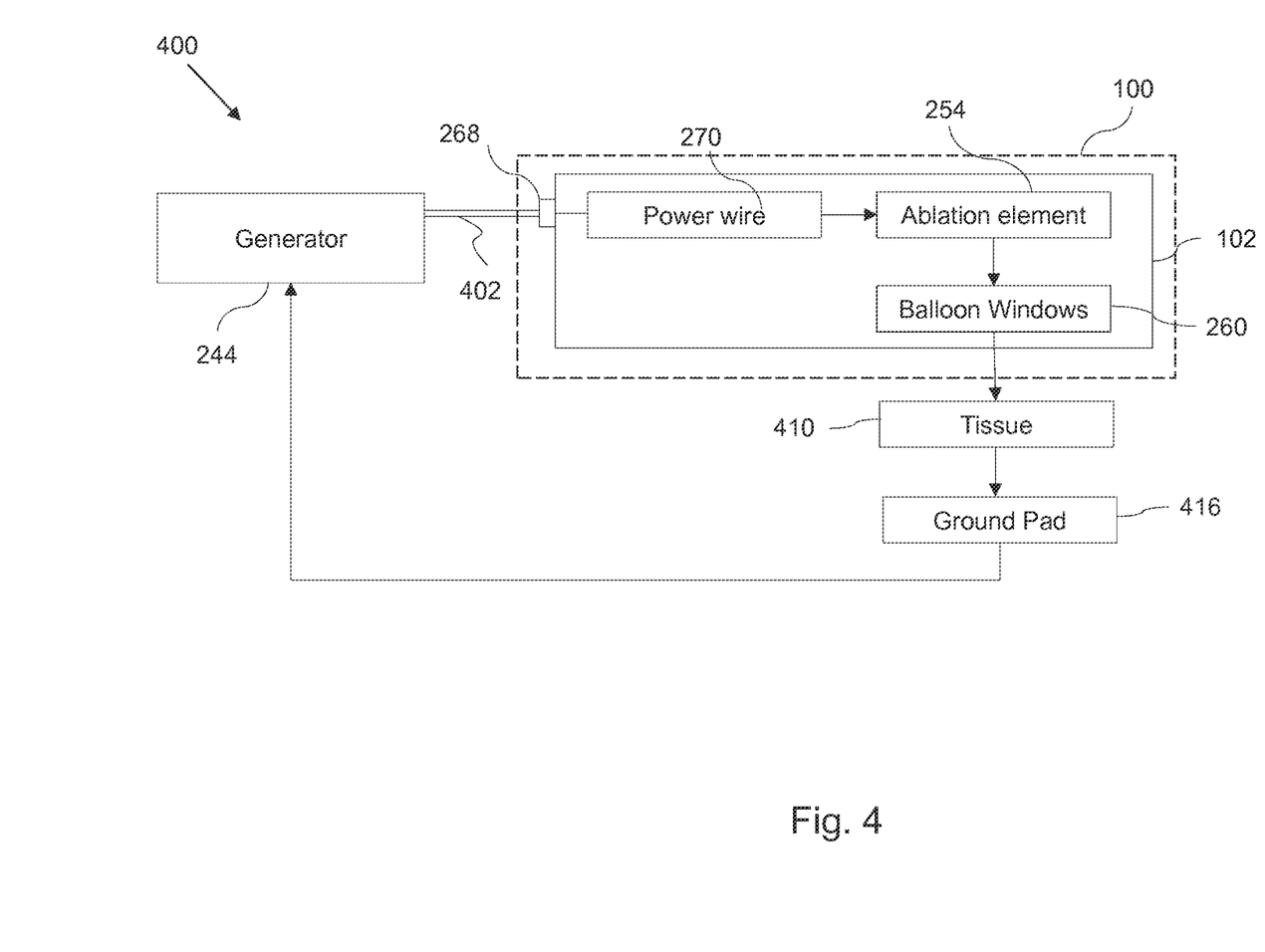
FIG. 4 is a circuit diagram illustrating the RF energy transfer within the catheter assembly.

Referring now to FIG. 4, a system 400 is illustrated for the transfer of RF energy within the catheter assembly 100. In an embodiment, the energy required for ablation can be provided to the catheter assembly 100 via an external Radio Frequency generator 244. In an embodiment, the RF generator 244 can be configured to provide RF energy to the catheter assembly 100. The energy generated by the RF generator 244 can be transferred to the catheter assembly 100 via a cable 402. In an embodiment, the cable 402 connects to the catheter assembly 100 via the jack 268. In an embodiment, the frequency of the RF energy generated by the RF generator 244 can be 460 KHz. The RF energy can be transferred to the power wire 270 located inside the catheter assembly 100 via the jack 268. In an embodiment, the power wire 270 can carry the RF energy to the RF transmitter 254 placed inside the balloon 104 of the catheter assembly 100. Further, the RF energy is converted to ionic energy in the fluid 242 where it is transferred to a tissue 410 via the plurality of balloon windows 260. In an embodiment, the plurality of balloon window 260 can be configured to carry the ionic energy generated at the RF transmitter 254 to the tissue 410 via the balloon 104.

In order to complete the electrical circuit through the tissue 410, a ground pad 416 must be attached intermediately to the patient.

A description of some exemplary embodiments of the invention can be contained in the following numbered paragraphs:

1. A catheter assembly for ablation of a target tissue comprising:
an elongated catheter body having a proximal end portion and a distal end portion, the elongated catheter body including:
a plurality of individual shafts placed concentric or adjacent to one another, the plurality of individual shafts each defining an interior wall and an exterior wall, wherein the interior wall of each of the plurality of individual shafts defines a respective lumen;
a balloon positioned at the distal end portion of the elongated catheter body and configured to be inflated between an expanded state and an unexpanded state with the use of a fluid flow along the lumen defined by at least one of the plurality of individual shafts;
an RF transmitter mounted on the exterior wall of at least one of the plurality of individual shafts such that the RF transmitter is conductively coupled with the balloon.

2. The catheter assembly of statement 1, wherein the plurality of individual shafts includes a first shaft, a second shaft, and a third shaft, each defining a length and cross-section area for controlled pressure drop within the assembly.

3. The catheter assembly of statement 2, wherein the first, second, and third shaft being placed concentrically with respect to one another from a central axis, the first shaft being the innermost, the second shaft being the middle, and the third shaft being the outermost shaft 4. The catheter assembly of statement 3, wherein an outside surface of the innermost shaft and an inside surface of the middle shaft define an inflow lumen for allowing fluid flow from the proximal end portion toward the balloon of the catheter assembly 5. The catheter assembly of statement 4, wherein an outside surface of the middle shaft and the inside surface of the outermost shaft define an outflow lumen for allowing fluid flow from the balloon toward the proximal end portion of the elongated catheter body.

6. The catheter assembly of statement 5, wherein the balloon includes an inflatable balloon having a proximal end portion and a distal end portion, the proximal end of the balloon being coupled to a distal end of the outside surface of the outermost shaft and the distal end of the balloon being coupled to a distal end of the outside surface of the innermost shaft.

7. The catheter assembly of statement 6, wherein the inflow lumen and the outflow lumen define a fluid flow path such that the fluid enters the proximal portion of the elongated catheter body and exits the distal portion of the balloon and filling the balloon and further configured to flow out via the outflow lumen, at least one of the plurality of shafts sized to define a controlled fluid inflow and outflow causing the balloon to inflate from the unexpanded state to the expanded state in a controlled manner.

8. The catheter assembly of statement 1, and further comprising an energy generator capable of supplying energy to the elongated catheter body and to the balloon.

9. The catheter assembly of statement 8, and further comprising an RF transmitter disposed within the balloon and configured to receive electrical energy from the energy generator.

10. The catheter assembly of statement 9, wherein the balloon includes a plurality of balloon windows wherein the RF transmitter is operably coupled to the plurality of balloon windows via a conductive fluid so as to transfer ionic energy to the plurality of balloon windows.

11. The catheter assembly of statement 9, further comprising a thermocouple wire positioned proximate to the ablation element and operably coupled to the ablation element so as to monitor a temperature of a fluid.

12. The catheter assembly of statement 3, wherein the innermost shaft is configured to receive a guide wire, the innermost shaft terminating at the distal end portion of the balloon and coupled thereat with the balloon.

13. The catheter assembly of statement 2, wherein the first shaft, second shaft, and third shaft being positioned adjacent one another.

14. The catheter assembly of statement 13, wherein a lumen defined by the wall of the first shaft defines a fluid inflow lumen, and a lumen defined by the wall of the second shaft defines a fluid outflow lumen.

15. The catheter assembly of statement 14, further comprising: a guide wire lumen configured to receive a guide wire, such that the guide wire lumen is defined by a wall in surface contact with the walls of the first shaft, second shaft, and third shaft externally.

16. A catheter assembly for ablation of a target tissue comprising:
an elongated catheter body having a proximal end portion and a distal end portion, the elongated catheter body including:
a first innermost shaft;
a second middle shaft;
a third outermost shaft, wherein the shafts are positioned independent and concentrically with respect to one another from a central axis, each of the shafts defining an interior wall and an exterior wall, wherein the interior wall of each of the shafts define a respective lumen; and
a balloon including an electrically insulative top coat on at least a portion of an outer surface of the balloon resulting in a plurality of balloon windows, the balloon positioned at the distal end portion of the elongated catheter body and configured to be inflated between an expanded state and an unexpanded state with the use of a fluid flow;
an RF transmitter mounted on the exterior wall of at least one of the plurality of individual shafts such that the RF transmitter is conductively coupled with the balloon via conductive fluid.

17. The catheter assembly of statement 16, and further comprising:
a power generator to supply energy to the elongated catheter body and the balloon.

18. The catheter assembly of statement 17, and comprising a RF transmitter configured for being conductively and operably coupled to the plurality of balloon windows so as to transfer ionic energy to the plurality of balloon windows via conductive fluid.

19. The catheter assembly of statement 18, and comprising a thermocouple positioned within the lumen of the middle shaft and operably coupled to the interior of the balloon so as to monitor a temperature of the fluid during outflow of the fluid.

20. The catheter assembly of statement 17, wherein the power generator is a radio frequency (RF) generator configured to supply RF energy to the RF transmitter.

The above disclosure is intended to be illustrative and not exhaustive. This description will suggest many variations and alternatives to a person of ordinary skill in this art. The various elements shown in the individual figures and described above can be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art can recognize other equivalents to the specific embodiment described herein which equivalents are intended to be encompassed by the claims attached hereto.

The invention claimed is:

1. A catheter assembly for ablation of a target tissue comprising:
    an elongated catheter body having a proximal end portion and a distal end portion, the elongated catheter body including:
        a plurality of individual shafts placed concentric or adjacent one another, the plurality of individual shafts each defining an interior wall and an exterior wall, wherein the interior wall of each of the plurality of individual shafts define a respective lumen;
        a balloon positioned at the distal end portion of the elongated catheter body and configured to be inflated between an expanded state and an unexpanded state with the use of a fluid flow along the lumen defined by at least one of the plurality of individual shafts; and
        an ablation element mounted on the exterior wall of at least one of the plurality of individual shafts such that the ablation element is conductively coupled with the balloon;
    wherein the plurality of individual shafts includes a first shaft, a second shaft, and a third shaft, each defining a length and cross-section area for controlled flow of the fluid;
    wherein the first, second, and third shaft being placed concentrically with respect to one another from a central axis, the first shaft being the innermost, the second shaft being the middle, and the third shaft being the outermost shaft; and
    wherein an outside surface of the innermost shaft and an inside surface of the middle shaft define an inflow lumen for allowing fluid flow from the proximal end portion toward the balloon of the catheter assembly.

2. The catheter assembly of claim 1, wherein an outside surface of the middle shaft and the inside surface of the outermost shaft define an outflow lumen for allowing fluid flow from the balloon toward the proximal end portion of the elongated catheter body.

3. The catheter assembly of claim 2, wherein the balloon includes an inflatable balloon having a proximal end portion and a distal end portion, the proximal end of the balloon being coupled to a distal end of the outside surface of the outermost shaft and the distal end of the balloon being coupled to a distal end of the outside surface of the innermost shaft.

4. The catheter assembly of claim 3, wherein the inflow lumen and the outflow lumen define a fluid flow path such that the fluid enters the proximal portion of the elongated catheter body, enters the proximal end portion of the balloon, and exits the distal portion of the balloon and further configured to flow out via the outflow lumen, at least one of the plurality of shafts sized to define a controlled outflow pressure drop causing the balloon to inflate from the unexpanded state to the expanded state in a controlled manner.

5. The catheter assembly of claim 4 wherein the controlled outflow pressure drop is controlled by a pressure control sensor in the balloon.

6. The catheter assembly of claim 4 wherein the controlled outflow pressure drop is controlled by an volumetric flow control that regulates flow of a fluid through the inflow lumen and the outflow lumen.

7. A catheter assembly for ablation of a target tissue comprising:
    an elongated catheter body having a proximal end portion and a distal end portion, the elongated catheter body including:
        a plurality of individual shafts placed concentric or adjacent one another, the plurality of individual shafts each defining an interior wall and an exterior wall, wherein the interior wall of each of the plurality of individual shafts define a respective lumen;
        a balloon positioned at the distal end portion of the elongated catheter body and configured to be inflated between an expanded state and an unexpanded state with the use of a fluid flow along the lumen defined by at least one of the plurality of individual shafts; and
        an ablation element mounted on the exterior wall of at least one of the plurality of individual shafts such that the ablation element is conductively coupled with the balloon;
    wherein the plurality of individual shafts includes a first shaft, a second shaft, and a third shaft, each defining a length and cross-section area for controlled flow of the fluid; and
    wherein the first shaft, second shaft, and third shaft being positioned adjacent one another.

8. The catheter assembly of claim 7, wherein a lumen defined by the wall of the first shaft defines a fluid inflow lumen, and a lumen defined by the wall of the second shaft defines a fluid outflow lumen.

9. The catheter assembly of claim 8, further comprising: a guidewire lumen configured to receive a guidewire, such that the guidewire lumen is defined by a wall in surface contact with the walls of the first shaft, second shaft, and third shaft externally.

10. The catheter assembly of claim 9 further comprising a rapid exchange port that connects the guidewire lumen to an external surface of the elongated catheter body.

11. The catheter assembly of claim 8, and further comprising:
  a power generator to supply energy to the elongated catheter body and the balloon.

12. The catheter assembly of claim 9, and comprising a RF transmitter configured for being conductively and operably coupled to the plurality of balloon windows so as to transfer ionic energy to the plurality of balloon windows via conductive fluid.

13. The catheter assembly of claim 10, and comprising thermocouple wires positioned within the lumen of the second middle shaft and operably coupled to the RF transmitter such as to monitor a temperature of the fluid inside the middle shaft during outflow of the fluid.

14. The catheter assembly of claim 9, wherein the power generator is a radio frequency (RF) generator configured to supply RF energy to the RF transmitter.

\* \* \* \* \*